(12) United States Patent
Iwabuchi et al.

(10) Patent No.: US 10,690,648 B2
(45) Date of Patent: Jun. 23, 2020

(54) LITHIUM REAGENT COMPOSITION, AND METHOD AND DEVICE FOR DETERMINING LITHIUM ION AMOUNT USING SAME

(71) Applicant: METALLOGENICS CO., LTD, Chiba (JP)

(72) Inventors: Takuya Iwabuchi, Chiba (JP); Tsugikatsu Odashima, Ichinoseki (JP)

(73) Assignee: METALLOGENICS Co., Ltd, Chiba (JP)

( * ) Notice: Subject to any disclaimer, the term of this patent is extended or adjusted under 35 U.S.C. 154(b) by 0 days.

(21) Appl. No.: 15/386,449

(22) Filed: Dec. 21, 2016

(65) Prior Publication Data
US 2017/0102371 A1 Apr. 13, 2017

Related U.S. Application Data

(63) Continuation of application No. 14/387,444, filed as application No. PCT/JP2012/061015 on Apr. 25, 2012, now Pat. No. 9,562,886.

(30) Foreign Application Priority Data

Apr. 6, 2012 (JP) ................. 2012-087928

(51) Int. Cl.
*G01N 33/20* (2019.01)
*C07D 487/22* (2006.01)
*G01N 31/22* (2006.01)

(52) U.S. Cl.
CPC ........... *G01N 33/20* (2013.01); *C07D 487/22* (2013.01); *G01N 31/22* (2013.01)

(58) Field of Classification Search
CPC ............................... G01N 33/84; G01N 31/22
See application file for complete search history.

(56) References Cited

U.S. PATENT DOCUMENTS

| 5,188,802 | A | 2/1993 | Schaeffer et al. |
| 2003/0186450 | A1* | 10/2003 | Balazs ............ G01N 33/84 436/79 |
| 2015/0276583 | A1 | 10/2015 | Iwabuchi |

FOREIGN PATENT DOCUMENTS

| JP | 05-178851 A | 7/1993 |
| JP | 11-046795 A | 2/1999 |

(Continued)

OTHER PUBLICATIONS

Synthesis of F28 Tetraphenylporphyrin and its Application to the Separation and Detection of Lithium Kenji Koyanagi and Masaaki Tabata Analytical Chemistry (Bunseiki Kagaku) vol. 51, No. 9,2002, pp. 803-807.*

(Continued)

*Primary Examiner* — Krishnan S Menon
*Assistant Examiner* — Dwan A Gerido
(74) *Attorney, Agent, or Firm* — Sughrue Mion, PLLC

(57) ABSTRACT

To provide to a reagent composition used in quantitative measurement of lithium in aqueous solutions such as biological specimens and environmental liquid samples by a simple colorimeter or ultraviolet-visible light spectrophotometer immediately, a reagent composition which permits to measure a concentration of lithium by visual observation, and a method and apparatus for measuring lithium ion by using the reagent. A reagent composition for measuring lithium comprising F28 tetraphenylporphyrin compound as chelating agent, including further a water-soluble organic solvent, a pH modifier and a stabilizer, and a method and apparatus for measuring lithium ion by using the reagent.

22 Claims, 5 Drawing Sheets

(56) References Cited

FOREIGN PATENT DOCUMENTS

| JP | 11-160313 A | 6/1999 |
|----|-------------|--------|
| JP | 2006-043694 A | 2/2006 |
| JP | 2006-242691 A | 9/2006 |

OTHER PUBLICATIONS

Kenji Koyamagi, et al., "Synthesis of F28 tetraphenyloporphyrin and its application to the separation and detection of lithium (I)", Department of Chemistry, Faculty of Science and Engineering, Saga University, 2002, pp. 803-807, vol. 51, No. 9.
International Search Report for PCT/JP2012/061015 dated Jun. 5, 2012, (PCT/ISA/210).

* cited by examiner

[Fig.1]
| base 3 mM lithium sample | | 1 time | 5 times | 10 times |
|---|---|---|---|---|
| Concentration of chelating reagent necessary to the final Li concentration at reaction | mM | 0.02 | 0.1 | 0.2 |
| Concentration of chelating reagent in the lithium reagent composition | mM<br>g/L | 0.08<br>0.1 | 0.38<br>0.4 | 0.75<br>0.8 |
[Fig.2]
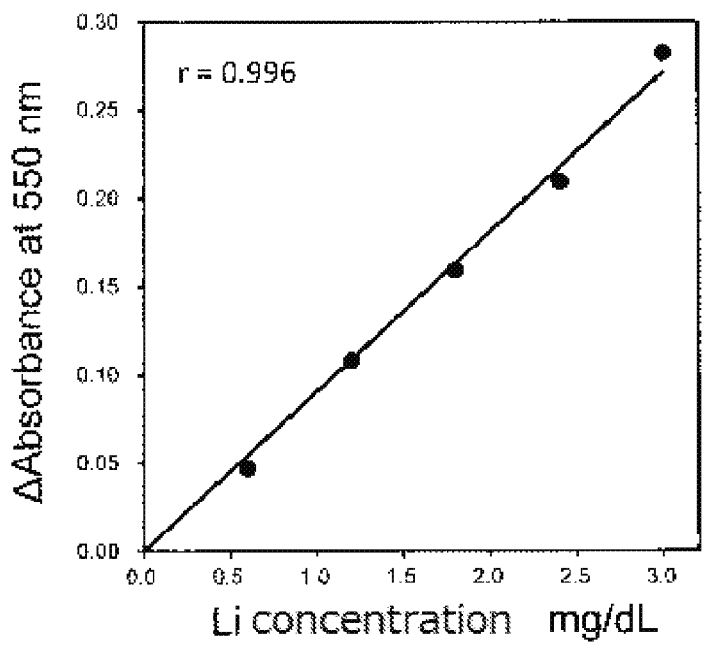
1 mg/dL ≒ 1.44 mM

[Fig.3]
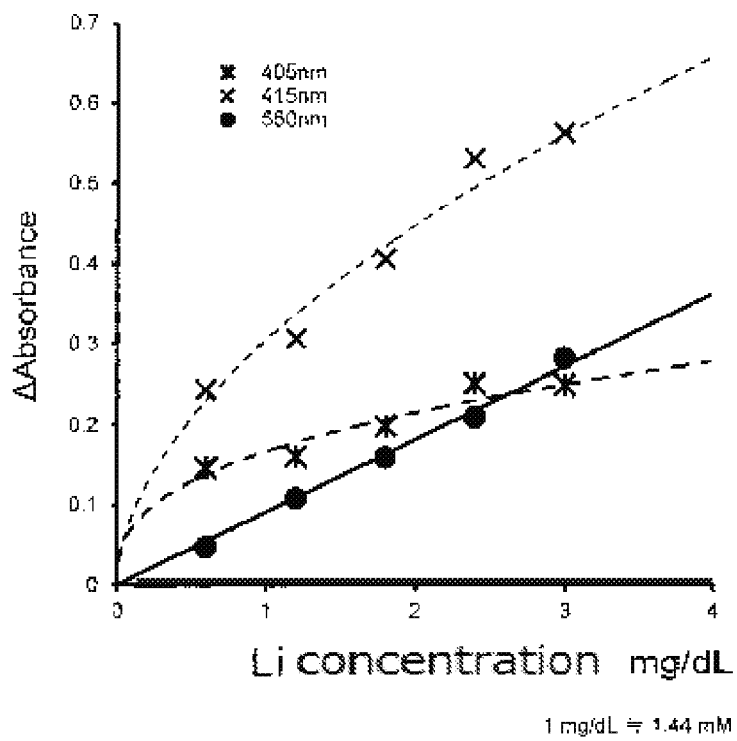
[Fig.4]
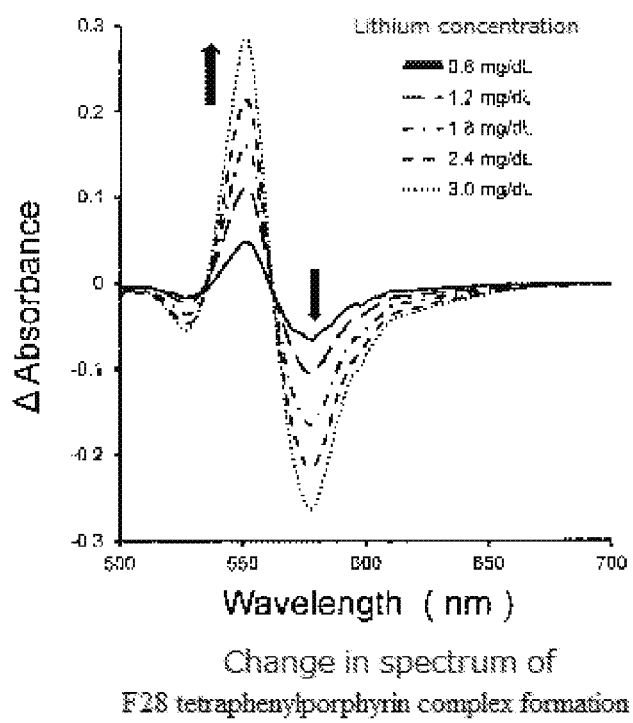
Change in spectrum of
F28 tetraphenylporphyrin complex formation

[Fig.5]
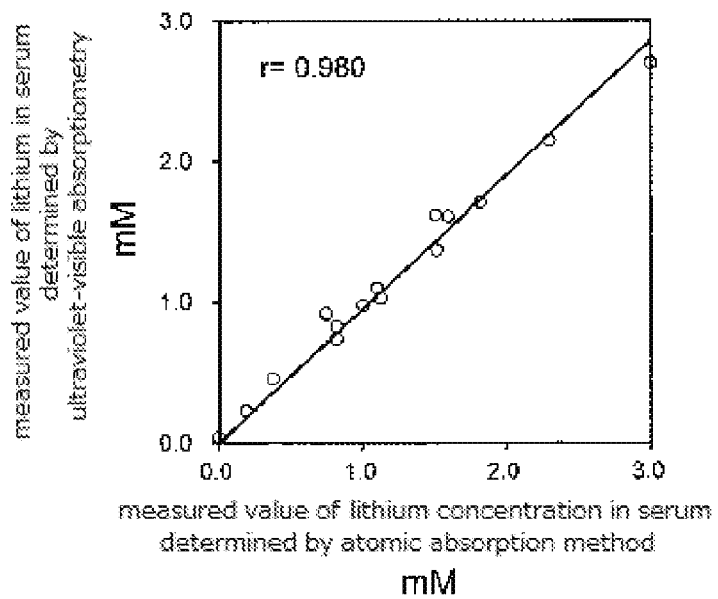
[Fig.6]
Table 1
Comparison to measured values obtained
by automatic analysis for control serum sample
unit : mM
| Control serum | Guaranteed value | Measured value obtained by the present invention |
|---|---|---|
| Precinorm U | 0.82 | 0.83 |
| Precipath U | 2.30 | 2.20 |
| Pathonorm | 1.51 | 1.50 |
| Autonorm | 1.00 | 0.99 |
automatic analyzer: Hitachi clinical analyer H-7700

[Fig.7]
Table 2
Lithium detection by naked eyes
| Color tone (standard sample) | Color |
|---|---|
| less than 1mM (normal region) | yellow |
| 1 to 2 mM (control region) | orange |
| more than 2 mM (abnormal region) | red |
| Control serum (specimen) | |
| Precinorm U (less than 1mM) | yellow |
| Pathnorm H (1.5 mM/L) | orange |
| Precipath U (2mM/L) | red |
[Fig.8]
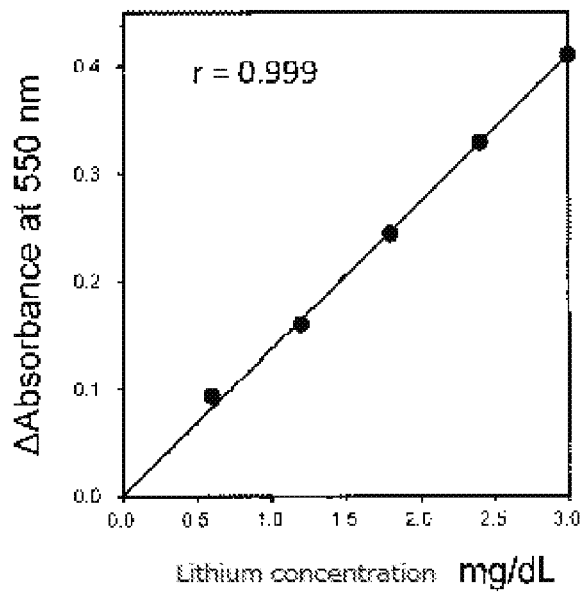
1 mg/dL ≒ 1.44 mM

[Fig.9]

Table 3
Comparison of measured values among different organic solvents
Unit: mM

|  | Atomic Absorption Method | Example 1 DMSO 20 wt % | Example 3 DMF 20 wt % | Example 4 DMA 20 wt % |
|---|---|---|---|---|
| Serum sample | 0.82 | 0.83 | 0.81 | 0.81 |

[Fig.10]

Table 4
Comparison of measured values among different stabilizers
Unit: mM

|  |  | Nonionic surfactant | anion surfactant | measured value |
|---|---|---|---|---|
| Example 5 | Sample 1 | (+) | (-) | 0.82 |
| Example 6 | Sample 2 | (-) | (+) | 0.83 |
| Example 7 | Sample 3 | (+) | (+) | 0.82 |

[Fig.11]

Table 5
Comparison of measured values among different masking agents
Unit: mM

|  |  | Triethanol amine | EDTA 2K | measured value |
|---|---|---|---|---|
| Example 5 | Sample 1 | (+) | (-) | 0.83 |
| Example 8 | Sample 2 | (-) | (+) | 0.83 |
| Example 9 | Sample 3 | (+) | (+) | 0.82 |

LITHIUM REAGENT COMPOSITION, AND METHOD AND DEVICE FOR DETERMINING LITHIUM ION AMOUNT USING SAME

This is a continuation of U.S. application Ser. No. 14/387,444, filed Dec. 1, 2014, which is a National Stage of International Application No. PCT/JP2012/061015, filed Apr. 25, 2012, claiming priority based on Japanese Patent Application No. 2012-087928, filed Apr. 6, 2012; the contents of which are incorporated herein by reference in their entirety.

TECHNICAL FIELD

This invention relates to a reagent composition used in quantitative measurement of lithium in an aqueous solution such as biological specimens and environmental liquid samples, and to method and device for determining the quantity of lithium ions by using the reagent composition.

BACKGROUND ART

It is known that lithium-containing drugs are effective in feeling stabilization and anti-depression, so that they are used widely as feeling-stabilizer and antidepressant drugs. Tablets of lithium carbonate (for oral administration) are generally prescribed as a feeling stabilizer as well as a drug for bipolar disorder (circulatory psychosis) or anti-depressive drug.

However, when such lithium-containing drug is administrated to patients, it is necessary to control or adjust the concentration of lithium in serum within a proper range. In fact, the lithium carbonate ($Li_2CO_3$) has such a characteristic that its administration effect is exhibited only when the concentration of lithium in blood arrives at nearly a "lithium poisoning level". In other words, when the drug is administrated, the therapeutic drug monitoring (TDM) is indispensable so as to monitor the lithium concentration in blood, since a therapeutic range is very near to the poison level.

In practice, it is necessary to control or limit the concentration of lithium in a patient blood sample within a limited range of generally from 0.6 to 1.2 mEq/L. In fact, when the lithium concentration in serum is lower than 0.6 mEq/L, no anti-depressive effect is expected. On the contrary, excess administration over 1.5 mEq/L of the concentration in plasma will result in the lithium poisoning. Overdose result in a fatal cause of symptoms of poisoning including tremor, alalia, nystagmus, renal disturbance and convulsion. Therefore, when a sign of latently dangerous symptoms of lithium-poisoning is observed, treatment with such lithium-containing drug must be stopped and the concentration in plasma must be re-measured so as to take a necessary measurement and to ease the lithium-poisoning.

Thus, the lithium salt is an effective medicine in the treatment of depressive patients, but overdose result in serious troubles. Therefore, when a lithium-containing anti-depressive drug is administered, it is indispensable to monitor the concentration of lithium in serum and to assure that the concentration is always kept with a limited range of from 0.6 to 1.2 mEq/L. Therefore, the quantitative measurement of lithium in serum is necessary in the treatment of depression patient.

Several liquid reagent compositions that permit colorimetric determination of lithium for the clinical laboratory test have been developed.

Patent Document 1 discloses a reagent composition used to measure the concentration of lithium in a biological sample by using primary color body cryptideinofa.

Patent Document 2 discloses an analytical reagent which reacts with lithium ion, comprising a macrocyclic compound having a pyrrole ring and eight bromine (Br) atoms combined at β position of the pyrrole ring.

Non-Patent Document 1 discloses that lithium ion can be detected by a compound in which all hydrogen bonded to carbons of tetraphenylporphyrin are replaced by fluorine.

LIST OF PRIOR ARTS

Patent Document 1 JP-A1-7-113807
Patent Document 2 EP 1283986-B1
Non-Patent Document 1 Analytical Chemistry Vol. 51, No. 9, pp. 803-807 (2002); K. Koyanagi et al., "Synthesis of F28 tetraphenylporphyrin and its use for separation and detection"

SUMMARY OF INVENTION

Problems to be Solved by the Invention

Known lithium reagent compositions, however, have such demerits or problems that they are poisonous compositions, that drug substances are expensive or are not supplied stably, and that most drug substances do not dissolve in water or, even soluble, deactivated in water, so that coloring reaction is very slow.

Above-mentioned non-Patent Document 1 was developed to solve the above problems and permits use of color developing technique. The method of this non-Patent Document 1, however, requires a dilution operation of a specimen since the sensibility is too high and the specification of the lithium reagent composition requires a range of over pH 11, so that it is easily deteriorated with $CO_2$ in air and hence measured data are not stable. Still more, no concentrated aqueous solution other than those of sodium hydroxide and of potassium hydroxide for a range of over pH11 is available in practice uses, so that it is difficult to keep a constant concentration. These concentrated aqueous solutions are hazardous substances which are difficult to handle so that use of which should be avoided. Their storage requires special containers and a larger scale special equipment or installation is required in their handling. Therefore, this technology is difficult to apply to on-site monitoring and POCT (Point Of Care Testing).

The reagent composition for measuring the quantity of lithium disclosed in Patent Document 1 is completely different from the present invention and can be used only at pH 12. As stated above, in a range of over pH 11, there is no concentrated aqueous solution in practice other than those of sodium hydroxide and of potassium hydroxide which is hazardous substances which are difficult to be handled and a larger scale special equipment or installation is required for their supplement.

The document of Koyanagi et al., of the non-Patent Document 1 teaches that lithium ion can be separated and detected by using F28 tetraphenylporphyrin. However, extraction with oily poisonous chloroform is necessary to perform the separation and detection of lithium ion. In fact, direct determination of lithium in aqueous solution without complicated pretreatment was impossible.

Thus, there was a problem that rapid and quantitative measurement of lithium ion in serum was impossible. In fact, detection of lithium ion in aqueous solutions by using F28 tetraphenylporphyrin is not easy so that quantitative measurement of lithium ion with this compound have not been realized until now.

This invention was made to solve the problem and provides a reagent composition used in quantitative measurement of lithium (concentration) in aqueous solutions such as biological specimens and environmental liquid samples, and to a measuring method and device using the reagent composition for determining the quantity of lithium ion. This invention permits to measure the concentration of lithium rapidly or immediately by using the conventional colorimeter. This invention provides also a lithium reagent composition which can be used for screening by visual observation and method and apparatus using the lithium reagent composition to measure lithium ion.

Means to Solve the Problems

A subject of this invention is a reagent composition for lithium ("lithium reagent composition" hereafter), characterized in that it comprises a compound having a structure represented by the formula (I):

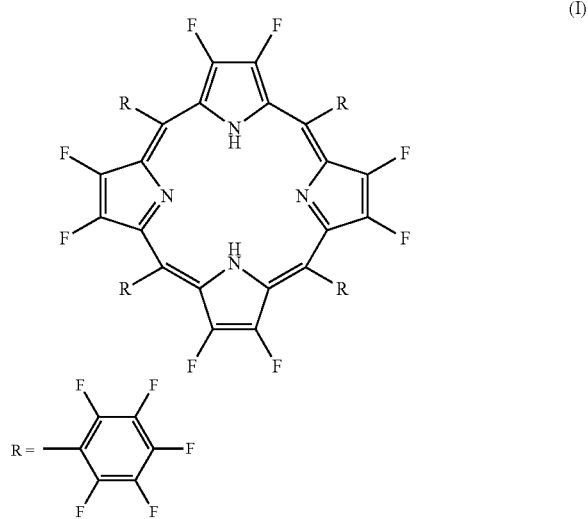

in which all hydrogens bonded to carbons of a tetraphenylporphyrin are replaced by fluorine, a water-soluble organic solvent and a pH modifier.

Lithium in an aqueous solution such as a biological specimen and an environmental sample generates a color with the lithium reagent composition according to the present invention, in particular with the above compound in which all hydrogens bonded to carbons of a tetraphenylporphyrin are replaced by fluorine, which functions as a chelating reagent (color developer).

Color change from yellow to red by a coloring reaction which is observed between a F28 tetraphenylporphyrin compound and lithium ions is difficult to be realized. However, what is requested is to determine precisely a quantity of lithium in serum in the range of 0.6 mg/dL to 2.0 mg/dL (0.9 mM to 3 mM). Inventors found such a fact that the quantity of lithium in serum can be determined precisely by setting a concentration of the F28 tetraphenylporphyrin compound in a range of 0.1 to 1.0 g/L, preferably 0.5 g/L in an embodiment of this invention.

The pH modifier is used preferably in the present invention. In fact, in an acidic side lower than pH 5.0, the F28 tetraphenylporphyrin compound which is a color developer (chelating reagent) according to this invention does not bond to lithium ion, so that no coloration change is observed and it is difficult to determine the quantity of lithium. In a range between pH 5 and pH 7, a specific reaction occurs between the color developer and lithium ion but the coloring reaction speed is slow. In a range between pH 8 and pH 11, the color developer reacts with lithium ion rapidly and a stable coloring complex can be formed. In alkaline side of higher than pH 11, a color tone of the chelating reagent and of coloring complex formed becomes instable in time. This may be caused by absorption of carbon dioxide in air, so that pH fluctuates. Therefore, it is necessary to use a pH modifier or pH buffer that can keep pH of the lithium reagent composition according to the present invention in a range from pH 7 to pH 12, preferably from pH 8 to pH 11.

The pH modifier can be selected from alkali medicine including sodium hydroxide, potassium hydroxide and ammonia, acid medicine including acetic acid, phosphoric acid, citric acid, carbonic acid, bicarbonic acid, oxalic acid, hydrochloric acid, nitric acid and their salts. The pH modifier may be pH buffer and may be selected from citric acid, carbonic acid, bicarbonic acid, phosphoric acid, succinic acid, phthalic acid, ammonium chloride, sodium hydroxide, potassium hydroxide, MES as Good's buffer, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, CAPS and their salts.

The lithium reagent composition according to the present invention permits the specific color reaction for lithium in a range of from pH 5 to pH 12 by incorporating the pH modifier.

It is indispensable that the solvent (polar solvent) used in this invention is an organic solvent that is compatible with water. The solvent can be a solution consisting mainly of organic solvent or an aqueous solution in which an organic solvent is added, provided that the solvent can be mixed uniformly with an aqueous solution such as serum, blood plasma and eluate which is a test sample. In fact, since a test sample to be measured is in a form of an aqueous solution when the concentration of lithium in sample is determined by a general-purpose type automated analyzer and by an ultraviolet-visible light spectrophotometer, it is desirable that the reagent composition is in a form of an aqueous solution.

The organic solvent is preferably chosen from dimethylsulfoxide (DMSO), dimethylformamide (DMF) and dimethylacetamide (DMA).

In actual products, a suitable stabilizer is incorporated in the reagent composition according to this invention. In an embodiment, a surfactant is used as the stabilizer. The surfactant improves the dispersibility of F28 tetraphenylporphyrin compound and prevents suspensions originated from the sample during the coloring reaction. Therefore, the stabilizer is used to assure such effect.

The stabilizer may be nonionic surfactant or anionic surfactant. The nonionic surfactant may be sorbitan fatty acid ester, pentaerythritol fatty acid part ester, propylene glycol monofatty acid ester, glycerin fatty acid monoester, polyoxyethylene alkyl ether, polyoxyethylene alkyl phenyl ether, polyoxyethylene polyoxypropylene glycol, polyoxyethylene fatty acid part ester, polyoxyethylene sorbitol fatty acid part ester, polyoxyethylene fatty acid ester, fatty acid di-ethanol amide, fatty acid ethanol amide, polyoxyethylene fatty acid amide, polyoxyethylene octylphenyl ether (Triton X-100 ®), p-nonyl phenoxy polyglycidol or their salts. Preferable nonionic surfactants are polyoxyethylene octylphenyl ether (Triton X-100 ®) and p-nonyl phenoxy polyglycidol.

The anionic surfactant as stabilizer may be alkyl sulfate ester salt, polyoxyethylene alkyl ether sulfate salt, polyoxyethylene phenyl ether sulfate salt, alkyl benzene sulfonate and alkane sulfonate. Typical anionic surfactant is selected from sodium dodecyl sulfate, sodium dodecyl benzene sulfonate and sodium polyoxyethylene alkylphenyl ether sulfate.

The lithium reagent composition according to the this invention can contain more than one masking reagent, in order to avoid disturbance caused by other ions than lithium, which may present in the sample, to suppress oxidation of the reagent composition and to improve the storage stability. The masking reagent may be not necessary if there are few ions other than lithium.

The masking reagent which can be added to the lithium reagent composition according to the present invention may be selected from triethanolamine, ethylenediamine, N,N,N', N'-tetrakis(2-pyridylmethylethylenediamine (TPEN), pyridine, 2,2-bipyridine, propylene diamine, dimethylene triamine, dimethylene triamine-N,N,N',N''',N'''-penta acetic acid (DTPA), trimethylene tetramine, trimethylene tetramine-N,N,N',N''',N'''',N''''-hexaacetic acid (TTHA), 1,10-phenanthroline, ethylene diamine tetraacetic acid (EDTA), O,O'-bis(2-aminophenyl)ethyleneglycol-N,N',N'-tetraacetic acid (BAPTA), N,N-bis(2-hydroxyethyl)glycine (Bicine), trans-1,2-diaminocyclohexane-N,N,N',N'-tetraacetic acid (CyDTA), O,O'-bis(2-aminoethyl)ethyleneglycol-N,N,N', N'-tetraacetic acid (EGTA), N-(2-hydroxyl)imino diacetic acid (HIDA), imino diacetic acid (IDA), nitrile triacetic acid (NTA), nitrile trimethylphosphonate (NTPO) and their salts. Triethanol amine is preferably used.

The lithium reagent composition according to this invention may include antiseptics to prevent degradation caused by microorganism. The antiseptics are not limited especially and may be sodium azide and Procline®. An amount of antiseptics is not especially limited and may be a concentration used generally as an antiseptic. For example, in case of sodium azide, the amount of antiseptics is about 0.1% by mass to a reaction solution. The antiseptics are usually prescribed for products which are stored for longer term duration.

To guarantee a long-term storage, the lithium reagent composition according to the present invention can be stored separately in a form of a kit for measuring lithium reagent comprising two separate reagents which are mixed just before measurement to realize the lithium reagent composition of claim 1. For example, a first reagent comprises the stabilizer and the pH modifier or pH buffer, while a second reagent comprises the tetraphenylporphyrin compound, water-miscible organic solvent, stabilizer and pH modifier or pH buffer.

In actual uses, the lithium reagent composition according to the present invention is contacted with a test sample of serum and/or blood plasma to induce coloring of the lithium complex which is measured in term of absorbance and spectrum so as to determine a quantity of lithium in the sample by comparing with reference concentrations of a standard sample whose lithium concentrations are of known.

In practice, in the coloring of the lithium complex and in its spectrum, the sensitivity is measured preferably at a wavelength of 550 nm or in the vicinity of wavelength from 530 nm to 560 nm, or the sensitivity is measured at a wavelength of 570 nm or in the vicinity of wavelength from 565 nm to 650 nm to calculate the concentration of lithium. In this case, the sensitivity is understood as the absorbance or a difference in absorbance in an ultraviolet-visible light spectrophotometer.

In the measuring device, the coloring, absorbance or spectrum of the lithium complex generated from the lithium reagent composition according to the present invention contacted with a test sample of serum and blood plasma is measured, or the sensitivity at a wavelength of 550 nm or in the vicinity of wavelength from 530 nm to 560 nm or the sensitivity at a wavelength of 570 nm or in the vicinity of wavelength from 565 nm to 650 nm is measured to calculate the quantitative value of lithium.

Advantages of Invention

The lithium reagent composition according to the present invention and the method and device for measuring lithium ions permit to determine or measure the concentration of lithium in an aqueous solution such as environmental sample and biological specimen easily. In the lithium reagent composition defined in claims 1 to 13, the calibration curve of the concentration of lithium is linear in a practical range of from 0.6 to 1.2 mEq/L, so that the concentration can be calculated by a simple operation from numerical values of the colorimeter and of the ultraviolet-visible light spectrophotometer. Therefore, the lithium concentration in serum sample or biological specimen can be determined quickly and quantitatively by usual spectrophotometer. The resulting data can be used as a management index in TDM treatment for example. Or, the quantitative determination of a larger number of specimens can be done in a short time by an automatic analyzer for clinical chemistry.

In the present invention, the lithium reagent composition is adjusted to a pH range of from pH 5 within pH 12 so as to enable measurement by the spectrometry. In an acidic range of under pH 5, the chelating reagent according to the present invention (F28 tetraphenylporphyrin lithium) does not bond to helium ions so that change in color which is dependent on the lithium concentration is not observed. On the contrary, in an alkaline side of over pH 12, a color tone of the chelating reagent and of coloring complex formed is not stable. The stability of the color tone becomes poor due to absorption of carbon dioxide in air which is a cause of pH fluctuation. In the pH range from pH 5 to pH 7, the specific coloring of the chelating reagent can be observed since the chelating reagent bonds to lithium ions but the coloring speed is too slow. Therefore, the pH range from pH 8 to pH 11 is preferable, since, in the pH range from pH8 to pH11, the chelating reagent bonds to lithium ion rapidly and coloring reaction is specific and stable.

Metal complex of tetraphenylporphyrin possesses a typical specific spectrum range in the vicinity from 380 nm to 460 nm called the "Soret band" in which the maximum sensitivity is obtained. This range may be selected as a measuring wavelength range. However, the sensitivity in this range is too high for a lithium concentration having clinical significance in a serum sample, so that dilution operation is necessary, resulting in increase of complicated operations and of additional units for dilution, which increase a size of measuring unit.

In the present invention, a wavelength of 550 nm or in the vicinity range of from 530 nm to 560 nm in which the sensitivity is lower by several times than that of the Soret band is used as the measuring wavelength range. By selecting this range, the optimum sensitivity is obtained for a concentration of sample to be tested and complicated dilution operation and dilution unit can be eliminated. Still more, the calibration curve according to the present invention has better linearity than that of in case of the Soret band, so that the concentration can be calculated easily from the measured values obtained by a small size colorimeter or an ultraviolet visible light spectrophotometer. Still more, change in color tone from yellow to red is very sharp in the present invention, the level of concentration can be judged by visual observation or naked eyes.

If the Soret band is used as a photometry wavelength, there is such another problem that the quantitative value of lithium is influenced by other organic substances and color components such as nitrate ion, creatinine, bilirubin, biliverdine and hemolyses hemoglobin. This influence or problem can be reduced in the present invention and the concentration of lithium can be determined with high precision.

In the conventional method for measuring lithium, a large scale single purpose apparatus was required. In this invention, the concentration of lithium can be determined by a small portable colorimeter and can be constructed as a POCT kit.

BRIEF DESCRIPTION OF DRAWINGS

FIG. 1 A table for calculating the optimum concentration of F28 tetraporphyrin according to this invention FIG. 2 Graphs of ultraviolet-visible light spectrophotometer obtained in the result of Example 1 according to this invention.

FIG. 3 Graph of the calibration curve at different wavelengths in Example 1 according to this invention.

FIG. 4 Graphs showing change in spectrum (color reaction) when F28 tetraphenylporphyrin-lithium complex is formed in Example 1 according to this invention.

FIG. 5 A graph showing a correlation between measured values of serum samples in Example 1 according to this invention and measured values obtained by the atomic absorption method (conventional method).

FIG. 6 [Table 1] showing a comparison with measured values obtained by using an automated analyzer in which the control serum samples were used.

FIG. 7 Table 2 showing how to detect lithium by visual observation in this invention.

FIG. 8 A graph of an absorbance spectrum in Example 1 according to this invention.

FIG. 9 [Table 3] showing measured values obtained by different organic solvents according to this invention.

FIG. 10 [Table 4] showing measured values obtained by different stabilizers according to this invention.

FIG. 11 [Table 5] showing measured values obtained by different masking reagents according to this invention.

MODE FOR CARRYING OUT THE INVENTION

Inventors studied lithium reagent compositions which can be used for measuring a concentration of lithium in serum and blood plasma quantitatively and more simply and focused on a compound represented by the general formula (I):

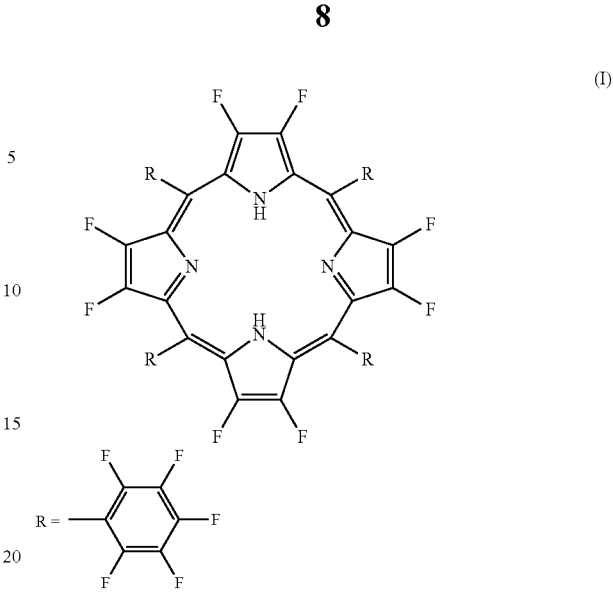

in which all of hydrogen atoms bonded to carbons of a tetraphenylporphyrin ring are replaced by fluorine atoms (the total number of fluorine is 28) in the macro cyclic compound disclosed in non-Patent Document 1 and complete the present invention. The above compound is called herein "F28 tetraphenylporphyrin".

Patent Documents 2 and 3 disclose similar lithium reagent compositions comprising a macro cyclic compound having pyrrole rings in which eight bromine atoms (Br) are boned to β position of the pyrrole ring, to provide an analytical reagent which can react with lithium ions. This compound, however, is difficult to react with lithium if pH is not in an alkali side above pH 11.

In case of the F28 tetraphenylporphyrin according to the present invention, the reaction occurs in a range of pH 5 to pH 12. In the present invention, the F28 tetraphenylporphyrin is used as a chelating reagent and is used to determine the lithium ions in an aqueous system quantitatively.

Now, the lithium reagent composition according to the present invention is explained in much in details by using Examples.

EXAMPLES

Example 1

Sample 1

In this Example 1, a first reagent as a pH buffer solution and a second reagent as a coloring reagent solution were prepared firstly. Then, two reagents of the first and second reagents were mixed just before measuring operation to prepare a lithium reagent composition according to the present invention. Although these two reagents can be stored in a form of mixer but it is advisable to store them separately and mix together just before measuring operation to avoid deterioration of the reagents during a long storage time duration.

Now, we will explain how to prepare the reagent composition according to the present invention in details.

To begin with, the first reagent (pH buffer solution) is prepared. Followings are the composition of the first reagent.

(1) First reagent (as stabilizer and buffer solution):
   chelating reagent: none
   organic solvent; none
   stabilizer (dispersant: nonionic surfactant): 1.0% by weight of
   TritonX-100 ® (polyoxyethylene octylphenyl ether)
   masking reagent: 10 mM of triethanol amine Into a mixture of above components, 7% by weight of ammonium chloride was added to adjust to pH 10. Then, the total volume was increased to 1 liter with purified water and stored in a usual storing container. If a proportion of TritonX-100 ® (polyoxyethylene octylphenyl ether) is lower than 1.0% by weight, turbidity may occur in some cases. On the contrary, if excess stabilizer is used, foam will be generated in a reactor vessel. Such turbidity or forming may influence the reproducibility of measurement, so that a range of range of 0.1 to 5.0% by weight is preferable and 1.0% by weight is more preferable.

In this Example, the masking reagent is 10 mM of triethanol amine. If an amount of the masking reagent is short, a satisfactory masking effect will not be obtained in such samples that contain excess foreign ions other than lithium. On the contrary, excess masking reagent will mask lithium ion itself, resulting in a cause of errors in measurement. Therefore, a range of 1.0 to 100 mM is preferable and 10 mM is more preferable.

The second reagent (color developing reagent solution) is produced as follows.

(2) Second reagent (as color developing reagent solution):
   chelating reagent: 0.5 g/L of F28 tetraphenylporphyrin
   organic solvent; 20% by weight of dimethylsulfoxide (DMSO)
   stabilizer (dispersant: nonionic surfactant): 1.0% by weight of TritonX-100 ® (polyoxyethylene octylphenyl ether)
   masking reagent: 10 mM of triethanolamine Into a mixture of above components, 0.05M (mol/L) of MOPS (Good's buffer) was added to adjust to pH 7.0. Then, the total volume was increased to 1 liter with purified water and the resulting solution was stored in a usual storing container.

In Example 1, color development reaction of F28 tetraphenylporphyrin compound is difficult. However, in the practical clinical laboratory test for measuring the concentration of lithium in serum, the accuracy in a lithium concentration range of 0.6 mM to 3 mM is required. Inventor found that the precise measurement can be done by selecting the concentration of F28 tetraphenylporphyrin compound to 0.1 to 1.0 g/L, preferably 0.5 g/L.

In the concentration range of lithium of 0.6 mM to 3 mM, measurement of lithium can be performed advantageously by setting the concentration of F28 tetraphenylporphyrin compound in the final reagent composition to 0.1 to 1.0 g/L, preferably 0.5 g/L. If the concentration is lower than the above limit, a reaction between F28 tetraphenylporphyrin and lithium ion is not sufficiently proceed. On the contrary, if the concentration exceeds the above limit, another trouble of increase in the absorbance of a blank of F28 tetraphenylporphyrin compound will occur. Therefore, the concentration of 0.5 g/L is preferably used.

In more details, the reaction between F28 tetraphenylporphyrin and lithium ion is a reaction of equal mole ratio of 1:1 to form a chelate complex. When a test sample containing 3 mM of lithium is reacted with the reagent composition according to the present invention under the condition of Example 1, the concentration of lithium in the reaction system becomes 0.02 mM. Therefore, the concentration of F28 tetraporphyrin compound must exist at a concentration of higher than 0.02 mM to effect the reaction sufficiently (neither too much nor too little).

In the complex-forming reaction (coloring reaction) between a chelating reagent and metal ions, it is necessary in general to use the chelating reagent (F28 tetraporphyrin) at an amount of from equal mol to ten times mols with respect to a reactant or a subject to be tested (lithium). As is shown in FIG. 1 which shows the optimum concentrations of F28 tetraporphyrin, the reagent composition is prepared in such a manner that the concentration of F28 tetraporphyrin during the reaction time becomes from equal mol to 10 times. In practice, it is preferable to use a concentration of the chelating reagent in the reagent composition of 0.5 g/L (5 times) rather than 0.1 g/L (same size) so as to permit to use in wider measuring conditions, because parameters of dosages at measuring reaction of an added amount of the reagent composition and of an amount of sample to be tested depend on measuring apparatus and desired thresholds and vary. For example, in case of a measuring apparatus whose measuring accuracy is not so high, an amount of sample may be increased to two times to five times to that of Example 1. To prepare to such cases, it is advisable to use the concentration of 0.5 g/L (5 times) of the reagent composition which is enough amount of reagent for the reaction. Excess amount of higher than 10 times has no advantage because increased amount of reagent may not significant advantage in the kinetic of coloring reaction but rather increase a trouble of elevation of blank level.

What is necessary is to satisfy the reaction condition in the mole ratio between chelating reagent and lithium. For example, when the concentration of chelating reagent (F28 tetraporphyrin) in the second reagent is 1.0 g/L, an amount of the second reagent which is added to the reaction can be reduced to a half. Or, when an amount of sample is reduced to a half, an amount of the chelating reagent can be reduced to a half.

In Example 1, the concentration of F28 tetraphenylporphyrin is 0.5 g/L. The optimum concentration of F28 tetraphenylporphyrin is 0.1 to 1.0 g/L that satisfies the reaction condition in mole and lowers to the minimum blank level.

An amount of dimethylsulfoxide (DMSO) is 5 to 30% by weight. When this amount is shorter, dispersion of F28 tetraphenylporphyrin in a solution become poor. On the contrary, if excess amount of dimethylsulfoxide result in increase of the organic solvent in the reagent composition. Therefore, a preferable amount is 20% by weight.

F28 tetraphenylporphyrin used in this Example 1 has a structure represented by the following formula (I):

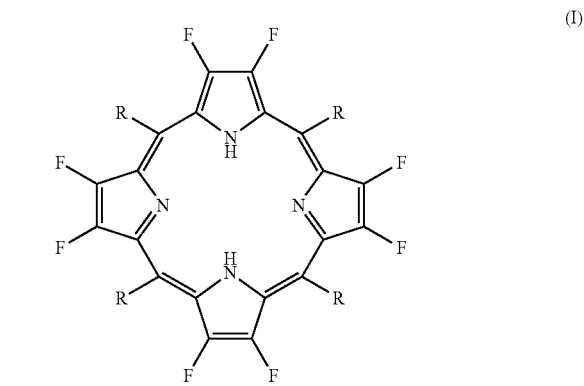

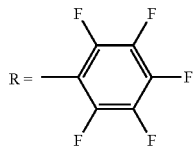

in which all hydrogens bonded to carbons of a tetraphenylporphyrin are replaced by fluorine atoms.

(3) Now, we will explain how to prepare a calibration curve of the lithium reagent composition prepared by mixing the first reagent with the second reagent for samples whose lithium concentrations are known.

In Example 1, 720 µL of the first reagent (buffer solution) and 240 µL of the second reagent (coloring reagent solution) were added to 6 µL of a sample. In this case, the first reagent has a buffer capacity at pH10. After the first and second reagents and the sample are mixed, the resulting mixture of a test liquid has about pH 10.

Thus, when F28 tetraphenylporphyrin according to the present invention is used as a chelating reagent, color developing reaction can be carried out in a pH range of from pH 5 to pH 10. In fact, the present invention provides a reagent for lithium measurement possessing a strong pH buffering action in a range of lower than pH 10, so that fluctuation of pH caused by absorption of $CO_2$ in air can be reduced. And hence, an adverse effect to measured values can be avoided, and it is possible to store the measuring reagents in general-purpose containers.

It is possible to mix the first reagent with the second reagent just before usage and to add the resulting mixture to the same volume of sample. In this case, 940 µL of the liquid mixture can be added to 6 µL of a sample.

A test sample was added to the resulting mixture of pH 10 to effect a reaction at ambient temperature for 10 minutes and then an absorbance at 550 nm was measured by a ultraviolet-visible light spectrophotometer (HITACHI, U-3900 type), the blank being the test sample. FIG. 2 shows the result which is a relation between absorbance and Li concentration (mg/L). FIG. 4 is a graph showing change in spectrum in a visible light range when F28 tetraphenylporphyrin-lithium complex is formed.

For metal complex of tetraphenylporphyrin, the maximum sensitivity is obtained at a wavelength range of so-called Soret band (about from 380 nm to 460 nm). However, in the present invention, this Soret band range is not used but a wavelength of 550 nm or in the vicinity range of from 530 nm to 560 nm is used, so that complicated operations of dilution and dilution means or an auxiliary facility are not necessary in the present invention.

FIG. 3 showing graphs of the calibration curves at different wavelengths reveals that better linearity in the calibration curve can be obtained when a wavelength of 550 nm or in the vicinity range of from 530 nm to 560 nm is used than cases when wavelengths of so-called Soret band are used. Therefore, the precise concentration can be calculated easily by a simple colorimeter or spectrophotometer. Still more, change in color from yellow to red is very sharp, so that a level of the concentration can be detected easily by naked eyes. In the conventional technique, an apparatus of a large scale for exclusive use is necessary to measure the lithium concentration, while, in the present invention, the lithium concentration can be measured easily by a portable colorimeter or ultraviolet-visual light spectrophotometer which is used widely. The present invention can be constructed in a form of a POCT kit.

In the graph of FIG. 3, a line (●) was obtained in a wavelength of 550 nm which was used in Example 1, while other two carves were obtained in wavelengths of 405 nm (*) and 415 nm (x) that corresponds to wavelengths of Soret band when the same procedure as Example 1 was repeated. In the cases of 405 nm (*) and 415 nm (x), however, measurement was carried out after the samples were diluted at 5 times since the sensitivity was too high. FIG. 3 reveals that a calibration curve having a good linearity can be obtained for the wavelength of 550 nm of Example 1, but the calibration curves of the wavelengths of 405 nm and 415 nm are not linear.

FIG. 4 shows changes in spectrum when F28 tetraphenylporphyrin-lithium complex is formed. It is confirmed clearly from FIG. 4 that the absorbance will increase linearly with the increase of lithium concentration from 6 mg/dL to 1.2 mg/dL, 1.8 mg/dL, 2.4 mg/dL and 3.0 mg/dL. An absorption peak of 415 nm (Soret band) which is typical for porphyrin-metal complex and an absorption peak of 550 nm (shown in FIG. 4) increase and an absorption peak of 570 nm (also shown in FIG. 4) decreases in proportion to the concentration of lithium. Therefore, a difference in absorbance can be calculated in these absorption peaks. In the present invention, the wavelength of 550 nm is preferably used as a photometry measuring wavelength because of good linearity in the calibration curve.

It is possible to select a wavelength range from 540 nm to 560 nm as the photometry measuring range in place of the wavelength of 550 nm used in Example 1. In fact, some measuring equipment may not have a photometry filter for 550 nm. In such case, the photometry measuring wavelength can be selected from a wavelength range in the vicinity such as 540 nm or 560 nm where the sensitivity is also high. A wavelength of 570 nm also can be used as a photometry measuring wavelength, since decrease in the sensitivity of absorbance at 570 nm is also quantitative as is shown in FIG. 4. Therefore, a difference in absorbance ($\Delta$ Abs) at 570 nm also can be calculated with a reference of the reagent as a blank.

In such a rare case that some contaminants that interfere at the wavelength of 550 nm are produced in a sample of patient and erroneous data are produced at the wavelength of 550 nm, it is possible to select a wavelength of 570 nm or in the vicinity of from 565 nm to 650 nm as photometry measuring wavelength to avoid such trouble and to calculate the lithium concentration from a decrease in the sensitivity as a difference in absorbance.

Now, we will explain experimental data of Example 1 which show that the lithium concentration can be measured at high accuracy with the lithium reagent composition of according to the present invention.

Results of Experiment by Ultraviolet-Visible Light Spectrophotometer (HITACHI, U-3900 Model)

FIG. 2 shows an experiment result measured by an ultraviolet-visible light spectrophotometer (HITACHI, U-3900 model). An axis of abscissa is known lithium ion concentrations (Li concentration, mg/dL) and an axis of ordinate is difference in absorbance measured by the ultraviolet-visible light spectrophotometer at a wavelength of 550 nm.

FIG. 2 reveals that a good linearity is obtained in a relation between the absorbance and the lithium concentration.

Correlation Test Between Atomic Absorption Method (Conventional Method) and the Method According to this Invention for a Serum Sample FIG. 5 is a graph showing a correlation of measured values between the measuring method of Example 1 according to this invention and the conventional atomic absorption method (conventional method) carried out for the same serum sample. Measured values obtained by the conventional atomic absorption method (conventional method) are plotted on axis of abscissa (X), while measured values according to this invention are plotted on axis of ordinate (Y). A regression line shown in FIG. 5 shows a good correlation of more than 95%. This result reveals that lithium in a serum sample can be determined quantitatively by an ultraviolet-visible light absorptiometry with the reagent composition according to the present invention.

Comparison of Measured Values Carried Out by Automatic Analysis for Control Serum Samples The lithium concentration was measured for following control serums samples in which the lithium concentration is valued:
Precinorm U (Roche)
Precipath U (Roche)
Pathonorm H (SERO AS)
Auto norm (SERO AS)

by using a biochemistry automated analyzer (HITACHI, H-7700 model) at a photometry measuring wavelength of 546 nm (which is a wavelength set in this analyzer and is near to 550 nm) by 1 point end method.

Device Parameters:
Reagent: 0.24 mL
Sample: 0.005 mL
Photometry wavelength (main/sub): 546 nm/700 nm
Measuring time: 10 minutes
Temperature: 37° C.
1 point end: increasing method Results shown in [Table 1] of FIG. 6 proves such a fact that that measured values obtained by the present invention coincide with the guaranteed values under the above conditions, so that it was confirmed that the lithium concentration in serums can be measured satisfactorily by an automated analyzer for clinical tests.

Detection of Lithium by Visual Observation

[Table 2] of FIG. 7 shows results of visual observation for test sample liquids. In this test, 920 μL of a coloring reagent solution which was a mixture of the first reagent and the second reagent according to the present invention was added to 8 μL of a test sample and the resulting mixture was reacted for 10 minutes at ambient temperature before the visual observation was effected. Developed colors were compared with a color tone guide prepared by using control serums in a form of the standard lithium concentration solutions at different concentration level of lithium.

Clear change in color from yellow to red was confirmed in respective concentration levels and the change in color of the control serums coincide with the color guide of the control serums. From this fact, it was proved or confirmed that the lithium concentration in serum can be determined quickly and easily without using specific equipment according to the present invention.

As explained above, it is confirmed that the lithium concentration can be measured at high accuracy by using the lithium reagent of Example 1 according to the present invention.

Example 2

Procedure of Example 1 was repeated but the first reagent in the lithium reagent composition was changed by adding 0.1 M (mol/L) of MOPS to adjust to pH 8.0 and by adding pure water up to the total volume of 1 liter. Namely, a mixture of the first reagent, the second reagent and the reagent was adjusted to nearly pH=8 at a measuring time.

(1) The first reagent (as stabilizer and buffer solution):
Chelating reagent: none
Organic solvent: none
Stabilizer (dispersant nonionic surfactant): Triton X-100 @ polyoxyethylene octylphenyl ether: 1.0% by weight
Masking agent: triethanol amine: 10 mM,
0.1M of MOPS was added to the above mixture to adjust pH of the mixture to pH 8. Then, the total volume was increased to 1 liter with purified water and the resulting solution was stored in a general purpose storing container.

(2) The second reagent (as a coloring reagent solution):
Chelating reagent: F28 tetraphenylporphyrin: 0.5 g/L
Organic solvent: Dimethylsulfoxide (DMSO): 20% by weight
Stabilizer (dispersant, nonionic surfactant): TritonX-100 @ (polyoxyethylene octylphenyl ether) 1.0% by weight
Masking agent: triethanolamine 10 mM To a mixture of above components, 0.05M of MOPS (buffer) was added to adjust pH to pH 7.0 and purified water was added up to the total volume of 1 liter, which was stored in a general-purpose container.

In the same manner as Example 1, 720 μL of the first reagent (buffer solution) of and 240 μL of the second reagent (coloring reagent solution) were added to 6 μL of a test sample at a time when the lithium concentration was measured. After the reaction was continued for 10 minutes at ambient temperature, the absorbency was measured at 550 nm wavelength by an ultraviolet-visible light spectrophotometer (HITACHI U-3900 type)

Experimental Result in the Ultraviolet-Visible Light Spectrophotometer (HITACHI U-3900 type)

FIG. 8 is a graph of the experimental result of the ultraviolet-visible light spectrophotometer (HITACHI, U-3900 type). The abscissa (X) is known lithium ion concentrations (Li concentration, mg/dL) and the ordinate (Y) plots differences in the absorbance at 550 nm in the ultraviolet-visible light spectrophotometer.

FIG. 8 reveals that the difference in absorbance is dependently proportional to the lithium concentration for the reagent composition prepared at pH 8 or under a measurement condition of pH 8 and that a good linearity of a calibration curve is obtained at pH 8 also.

However, at the measurement condition of pH 8, the reaction kinetics a little slows down and is quantitatively stabilized in about 10 minute to 20 minutes. In case of pH 10, the reaction completes within 10 minutes. Therefore, in the buffer system in a range of pH 5 to pH 10 of lithium reagent composition of this invention, there is no necessity to use a buffer system of above pH 11 based on a thick hydroxide solution such as sodium hydroxide and potassium hydroxide in case, and hence handling operation becomes simpler. The pH range can be set according to desired needs and is adjusted preferably to pH 10 in which the reaction kinetics is rapid and sufficient buffer power can be maintained with Good's buffer, ammonium chloride system and carbonic acid system. From a practical point of view, it is advisable to carry out with a pH 10 buffer system of Example 1 in which the reaction advances accurately.

Thus, in the lithium reagent composition according to this invention, it is necessary to use a pH buffer which functions as pH modifier for adjusting pH to a range from 7 to 12 or a pH buffer as pH modifier. More desirably, it is preferable to use a pH modifier or pH buffer which adjusts pH to pH 8 to pH 11, and more preferably to use a pH modifier or pH buffer which adjust pH around pH 10.

Example 3

Now, selection of the organic solvent will be explained. In the invention, it is important that the solvent is an organic solvent which is miscible with water since the reaction solutions to be measured are aqueous solutions such as serum. The solvent can be a liquid consisting mainly of an organic solvent or an aqueous solution containing an organic solvent, provided that the components in the reagent composition are stabilized as an aqueous solution. In particular, when the lithium concentration in the sample is measured by a general-purpose automated analyzer and by an ultraviolet-visible light spectrophotometer, it is desirable to use basically an aqueous solution containing organic solvent.

Other organic solvents which can be mix with water than Examples 1, 2 are explained in Example 3. In Example 3, the same procedure as Example 1 was repeated but the organic solvent of the second reagent of dimethylsulfoxide (DMSO) (20% by weight) in the lithium reagent composition was replaced by dimethylformamide (DMF) (20% by weight).

(1) The first reagent (as buffer solution):
    Chelating reagent: none
    Organic solvent: none
    Stabilizer (dispersant: nonionic surfactant): TritonX-100 ® (polyoxyethylene octylphenyl ether) 1.0% by weight
    Making reagent: triethanolamine 10 mM,
Into a mixture of above components, 7% by weight of ammonium chloride was added to adjust pH to pH 10 and purified water was added up to the total volume of 1 liter, which was stored in a general-purpose container.

(2) The second reagent (as coloring reagent solution)
    Chelating reagent: F28 tetraphenylporphyrin: 0.5 g/L
    Organic solvent: Dimethylformamide (DMF): 20% by weight
    Stabilizer (dispersing agent: nonionic surfactant) TritonX-100® (polyoxyethylene octylphenyl ether) 1.0% by weight
    Masking reagent: triethanolamine 10 mM
Into a mixture of above components, 0.05M of MOPS (buffer) was added to adjust pH to pH 7.0 and purified water was added up to the total volume of 1 liter, which was stored in a general-purpose container.

Example 4

As the organic solvent which is miscible with water, dimethylsulfoxide (DMSO) (20% by weight) was used in Example 1 and dimethylformamide (DMF) (20% by weight) was used in Example 2.

In this Example 4, a lithium reagent composition was prepared by using dimethylacetamide (DMA) (20% by weight) as an organic solvent which is miscible with water and the concentration of lithium was measured by the lithium reagent composition.

(1) The first reagent (as buffer solution):
    Chelating reagent: none
    Organic solvent: none
    Stabilizer (dispersant: nonionic surfactant): TritonX-100 ® (polyoxyethylene octylphenyl ether) 1.0% by weight
    Making reagent: triethanolamine 10 mM,
Into a mixture of above components, 7% by weight of ammonium chloride was added to adjust pH to pH 10 and purified water was added up to the total volume of 1 liter, which was stored in a general-purpose container.

(2) The second reagent (as coloring reagent solution)
    Chelating reagent: F28 tetraphenylporphyrin: 0.5 g/L
    Organic solvent: dimethylacetamide (DMA): 20% by weight
    Stabilizer (dispersing agent: nonionic surfactant) TritonX-100 ® (polyoxyethylene octylphenyl ether) 1.0% by weight
    Masking reagent: triethanolamine 10 mM
Into a mixture of above components, 0.05M of MOPS (buffer) was added to adjust pH to pH 7.0 and purified water was added up to the total volume of 1 liter, which was stored in a general-purpose container.

FIG. 9 shows the results of a comparison of lithium detected in the control serum sample, in which the concentration of lithium was measured by the same procedure as Example 1 but the organic solvent was changed from Dimethylsulfoxide (DMSO) of Example 1 to dimethylformamide (DMF) in Example 3 and to dimethylacetamide (DMA) in Example 4. [Table 3] of FIG. 9 shows results of a comparison between the conventional measuring method and the measuring method according to the present invention.

[Table 3] of FIG. 9 showing "Comparison among different organic solvents" shows following results: a measured value obtained by using dimethylformamide (DMF)(20% by weight) as organic solvent which is miscible with water in Example 1 was 0.83 mM (mmol/L); a measured value obtained by using dimethylformamide (DMF) (20% by weight) as organic solvent which is miscible with water in Example 3 was 0.82 mM (mmol/L); and a measured value obtained by using dimethylacetamide (DMA) (20% by weight) as organic solvent which is miscible with water in Example 4 was 0.81 mM (mmol/L). These values coincide over 95% with a measured value obtained by atomic absorption spectrophotometry 0.82 mM (mmol/L). Therefore, it is possible to determine quantitatively and accurately the concentration of lithium in aqueous samples such as serum by dispersing F28 tetraphenylporphyrin uniformly in these organic solvents to prepare the liquid reagent composition according to the present invention.

Example 5

In this Example 5, selection of stabilizer for the lithium reagent composition according to the present invention is explained.

Use of stabilizers for the lithium reagent compositions in Examples 5 to 7 is basically same as Example 1 but the stabilizer was changed to nonionic surfactant alone (Example 5), anionic surfactant (Example 6) and both of nonionic surfactant and anionic surfactant (Example 7) respectively.

In following Example 5, the lithium reagent composition contains only nonionic surfactant (TritonX-100®)) (polyoxyethylene octylphenyl ether) as the stabilizer. Other components in the lithium reagent composition are same as Example 1.

Example 5

(1) The first reagent (as buffer solution):
    Chelating reagent: none
    Organic solvent: none
    Stabilizer (dispersant: nonionic surfactant): TritonX-100 ® (polyoxyethylene octylphenyl ether) 1.0% by weight
    Making reagent: triethanolamine 10 mM Into a mixture of above components, 7% by weight of ammonium chloride was added to adjust pH to pH 10 and purified water was added up to the total volume of 1 liter, which was stored in a general-purpose container.
(2) The second reagent (as coloring reagent solution)
    Chelating reagent: F28 tetraphenylporphyrin: 0.5 g/L
    Organic solvent: Dimethylsulfoxide (DMSO): 20% by weight
    Stabilizer (dispersing agent: nonionic surfactant) TritonX-100® (polyoxyethylene octylphenyl ether) 1.0% by weight
    Masking reagent: triethanolamine 10 mM
Into a mixture of above components, 0.05M of MOPS (buffer) was added to adjust pH to pH 7.0 and purified water was added up to the total volume of 1 liter, which was stored in a general-purpose container.

Example 6

In Example 6, the composition contains only anionic surfactant (sodium dodecyl sulfate (Wako Junyaku).
(1) The first reagent (as buffer solution):
    Chelating reagent: none
    Organic solvent: none
    Stabilizer (dispersant: anionic surfactant only):
        sodium dodecyl sulfate (Wako Junyaku) 1.0% by weight
    Making reagent: triethanolamine 10 mM,
Into a mixture of above components, 7% by weight of ammonium chloride was added to adjust pH to pH 10 and purified water was added up to the total volume of 1 liter, which was stored in a general-purpose container.
(2) The second reagent (as coloring reagent solution)
    Chelating reagent: F28 tetraphenylporphyrin: 0.5 g/L
    Organic solvent: Dimethylsulfoxide (DMSO): 20% by weight
    Stabilizer (dispersing agent: anionic surfactant only) (sodium dodecyl sulfate (Wako Junyaku) 1.0% by weigh
    Masking reagent: triethanolamine 10 mM
Into a mixture of above components, 0.05M of MOPS (buffer) was added to adjust pH to pH 7.0. Then, the total volume was increased to 1 liter with purified water and the resulting solution was stored in a general-purpose storing container.

Example 7

In Example 7, the composition contains both of anionic surfactant and of nonionic surfactant as stabilizer in the lithium reagent composition.
(1) The first reagent (as buffer solution):
    Chelating reagent: none
    Organic solvent: none
    Stabilizer (dispersant: nonionic surfactant and anionic surfactant):
        (a) nonionic surfactant: TritonX-100® (polyoxyethylene octylphenyl ether) 1.0% by weight
        (b) anionic surfactant: sodium dodecyl sulfate (Wako Junyaku) 1.0% by weigh
    Making reagent: triethanolamine 10 mM,
Into a mixture of above components, 7% by weight of ammonium chloride was added to adjust pH to pH10. Then, the total volume was increased to 1 liter with purified water and the resulting solution was stored in a general-purpose storing container.
(2) The second reagent (as coloring reagent solution)
    Chelating reagent: F28 tetraphenylporphyrin: 0.5 g/L
    Organic solvent: Dimethylsulfoxide (DMSO): 20% by weight
    Stabilizer (dispersing agent: nonionic surfactant and anionic surfactant)
        (a) nonionic surfactant: TritonX-100® (polyoxyethylene octylphenyl ether) 1.0% by weight
        (b) anionic surfactant: sodium dodecyl sulfate (Wako Junyaku) 1.0% by weigh
    Masking reagent: triethanolamine 10 mM
Into a mixture of above components, 0.05M of MOPS (buffer) was added to adjust pH to pH 7.0. Then, the total volume was increased to 1 liter with purified water and the resulting solution was stored in a general-purpose storing container.

The concentration of lithium in the control serum sample was determined quantitatively by the same procedure as Example 1 by using lithium reagent compositions prepared in Example 5, Example 6 and Example 7. Results are summarized in [Table 4] of FIG. 10 "Comparison of measured values among different stabilizers".

FIG. 10 reveals that measured values coincide over 95% among a measured value for the nonionic surfactant alone (0.82 mM), a measured value for anionic surfactant alone (0.82 mM) and a measured value for two surfactants (0.83 mM).

This result shows that almost same measured values can be obtained regardless of surfactant type used or their combination. Therefore, the surfactants can be used in combined for a sample in which suspension or turbidity is worried about.

Now, selection of the masking reagent for the lithium reagent composition is explained. In above-mentioned Examples, triethanolamine was used as a masking reagent for the lithium reagent composition, but ethylenediamine tetra acetic acid (EDTA) also can be used.

Example 5 shows a case of a lithium reagent composition containing triethanolamine as masking reagent, Example 8 shows a case of ethylenediamine tetraacetic acid (EDTA) alone and Example 9 shows a case containing both masking reagents.

Example 8

In Example 8, potassium ethylenediamine tetraacetic acid (EDTA, 2K) alone was used as a masking reagent.
(1) The first reagent (as buffer solution):
    Chelating reagent: none
    Organic solvent: none
    Stabilizer (dispersant: nonionic surfactant): TritonX-100® (polyoxyethylene octylphenyl ether) 1.0% by weight
    Making reagent: ethylenediamine tetra acetic acid (EDTA 2K) (Dojin Chemical) 10 mM
Into a mixture of above components, 7% by weight of ammonium chloride was added to adjust pH to pH10 and purified water was added up to the total volume of 1 liter, which was stored in a general-purpose container.
(2) The second reagent (as coloring reagent solution)
    Chelating reagent: F28 tetraphenylporphyrin: 0.5 g/L
    Organic solvent: Dimethylsulfoxide (DMSO): 20% by weight
    Stabilizer: TritonX-100® (polyoxyethylene octylphenyl ether): 1.0% by weight
    Masking reagent: ethylenediamine tetra acetic acid (EDTA 2K) (Dojin Chemical): 10 mM
Into a mixture of above components, 0.05M of MOPS (buffer) was added to adjust pH to pH 7.0. Then, the total volume was increased to 1 liter with purified water and the resulting solution was stored in a general-purpose storing container.

Example 9

In Example 9, both of triethanolamine and ethylenediamine tetraacetic acid (EDTA 2K) are used in combination as a masking reagent.
(1) The first reagent (as buffer solution):
  Chelating reagent: none
  Organic solvent: none
  Stabilizer (dispersant: nonionic surfactant):
    TritonX-100® (polyoxyethylene octylphenyl ether): 1.0% by weight
  Making reagent: triethanolamine 10 mM
Into a mixture of above components, 7% by weight of ammonium chloride was added to adjust pH to pH 10 and purified water was added up to the total volume of 1 liter, which was stored in a general-purpose container.
(2) The second reagent (as coloring reagent solution)
  Chelating reagent: F28 tetraphenylporphyrin: 0.5 g/L
  Organic solvent: Dimethylsulfoxide (DMSO): 20% by weight
  Stabilizer: TritonX-100® (polyoxyethylene octylphenyl ether) 1.0% by weight
  Masking reagent:
    triethanolamine: 10 mM
    ethylenediamine tetraacetic acid (EDTA 2K) (Dojin Chemical): 0.1 mM
Into a mixture of above components, 0.05M of MOPS (buffer) was added to adjust pH to pH 7.0. Then, the total volume was increased to 1 liter with purified water and the resulting solution was stored in a general-purpose storing container.

The concentration of lithium in the control serum sample was determined quantitatively by the same procedure as Example 1 by using lithium reagent compositions prepared in Example 8 and Example 9. Results are summarized in [Table 5] of FIG. 11 "Comparison of measured values among different masking agents".

FIG. 11 reveals that measured values coincide over 95% for among a measured value for triethanolamine alone (0.83 mM), a measured value for ethylenediamine tetra acetic acid (EDTA) alone (0.83 mM) and a measured value for their combination use (0.82 mM).

This result shows that almost same measured values can be obtained regardless of type of masking agent used or their combination. Therefore, suitable masking agent(s) can be used to prevent degradation of the reagent caused by trace metal ions which may be contained in a stocked reagent. The masking agent can be used for a test sample containing excess inclusion ions.

As explained above Examples according to this invention, the concentration of lithium in aqueous solution such as environmental sample and biological specimen can be determined by the convenient colorimeter and can be judged immediately by visual observation.

A scope of this invention should not be limited to the Examples but is defined by claims. Details of Examples can be changed, altered and modified provided that the characteristic of this invention is not impaired. For example, in Examples 1-9, the reagent composition for determining the concentration of lithium is divided into two reagents of the first and second reagents separately to store the reagent composition for a longer term. However, if measurement is carried out within a short period, the first reagent and the second reagent can be mixed from the beginning and the resulting mixture is used in the measurement.

The invention claimed is:

1. A lithium reagent composition for measuring the quantity of lithium in serum or blood plasma, comprising a compound having a structure represented by the formula (I):

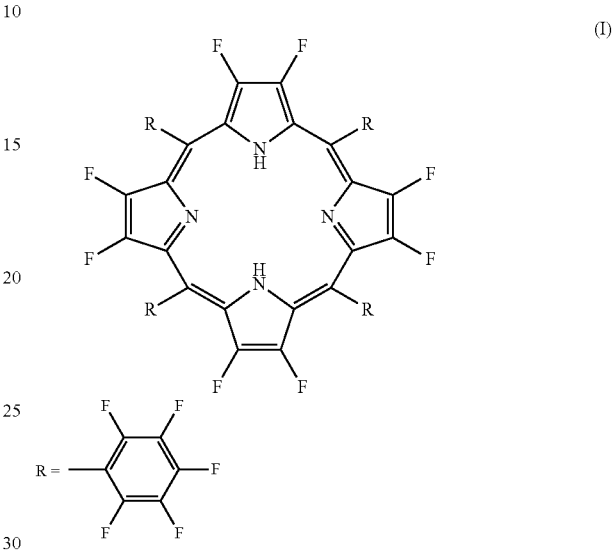

in which all hydrogens bonded to carbons of a tetraphenylporphyrin are replaced by fluorine atoms, a water-miscible organic solvent selected from the group consisting of dimethylsulfoxide (DMS), dimethylformamide (DMF) and dimethylacetamide (DMA), and a pH modifier for adjusting the pH to a range from pH 5 to pH 12,
wherein said reagent composition is an aqueous solution.

2. The lithium reagent composition of claim 1, in which said pH modifier is selected from acids including hydrochloric acid, nitric acid, acetic acid, phosphoric acid, citric acid, carbonic acid, bicarbonic acid, oxalic acid and their salts, alkali medicine including sodium hydroxide, potassium hydroxide, ammonia and their salts.

3. The lithium reagent composition of claim 1, in which said pH modifier is pH buffer.

4. The lithium reagent composition of claim 3, in which said pH buffer is selected from citric acid, carbonic acid, bicarbonic acid, phosphoric acid, succinic acid, phthalic acid, ammonium chloride, sodium hydroxide, potassium hydroxide, MES as Good buffer, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, CAPS and their salts.

5. The lithium reagent composition of claim 3, in which the reagent composition develops a color reaction for lithium in a range from pH 5 to pH 11.

6. The lithium reagent composition of claim 1, including further a stabilizer.

7. The lithium reagent composition of claim 1, in which said stabilizer is nonionic surfactant and/or anionic surfactant.

8. The lithium reagent composition for lithium according to claim 7, in which said nonionic surfactant is selected from esters of sorbitan fatty acid, partial esters of pentaerythritol fatty acid, esters of propylene glycol fatty acid, glycerin fatty acid monoester, polyoxyethylene alkyl ether, polyoxyethylene alkyl phenyl ether, polyoxyethylene polyoxypropyleneglycol, partial esters of polyoxyethylene fatty acid, partial esters of polyoxyethylene sorbitol fatty acid, esters of polyoxyethylene fatty acid, fatty acid di-ethanol amide, fatty acid monoethanol amide, polyoxyethylene fatty acid amide, polyoxyethylene octylphenyl ether (TritonX-100®), p-nonyl phenoxypolyglycidol and their salts.

9. The lithium reagent composition for lithium according to claim 7, in which said anionic surfactant is alkyl sulfate ester salt, polyoxyethylene alkyl ether sulfate salt, alkylbenzenesulfonate salts and alkanesulfonat.

10. The lithium reagent composition from lithium according to claim 9, wherein the anionic surfactant is sodium dodecyl sulfate, sodium dodecyl benzene sulfonate, sodium polyoxyethylene alkly phenyl ether sulfate or salts thereof.

11. The lithium reagent composition for lithium according to claim 1, including further a masking reagent.

12. The lithium reagent composition for lithium according to claim 11, in which said masking reagent is chosen from triethanolamine, ethylenediamine, N,N,N',N'-tetrakis(2-pyridylmethl)ethylenediamine (TPEN), pyridine, 2,2-bipyridine, propylenediamine, diethyl enetriamine, diethylenetriamine-N,N,N,N'',N''-pentaacetate (DTPA), triethylenetetramine, triethylenetetramine-N,N,N',N'',N''',N'''-hexaacetate (TTHA), 1,10-phenanthroline, ethylenediamine tetraacetate (EDTA), O,O'-bis(2-aminophenyl)ethyleneglycol-N,N,N,N-tetraacetate (BAPTA), N,N-bis(hydroxyethyl)glycine (Bicine), trans-1,2-diaminocyclohexane-N,N,N,N-tetraacetate (CyDTA), O,O'-bis(2-aminoethyl)ethyleneglycol-N,N',N-tetraacetate (EGTA), N-(2-hydroxyl)iminodiacetate (HIDA), imino diacetic acid (IDA), nitrile triacetic acid (NTA), nitrylo tris-methylphosphonate (NTPO) and their salts.

13. The lithium reagent composition for lithium according to claim 1, in which the coloring of the lithium complex is measured by the sensitivity in the spectrum at a wavelength of 570 nm.

14. The lithium reagent composition of claim 1, wherein a coloring is measured at a wavelength of 530 nm to 560 nm.

15. The lithium reagent composition of claim 14, wherein the wavelength range is 550 nm.

16. The lithium reagent composition for lithium according to claim 1, in which the coloring of the lithium complex is measured by the sensitivity in the spectrum in a wavelength range from 565 nm to 650 nm.

17. A lithium reagent kit comprising a first reagent comprising the stabilizer and the pH modifier defined in claim 1, and a second reagent including the compound having the structure represented by the formula (I):

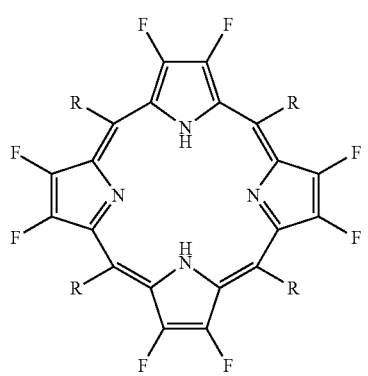

(I)

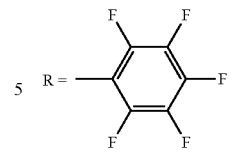

in which all hydrogens bonded to carbons of a tetraphenylporphyrin are replaced by fluorine atoms, the water-soluble organic solvent, selected from the group consisting of dimethylsulfoxide (DMSO), dimethylformamide (DMF) and dimethylacetamide (DMA), said first and second reagents being stored separately and mixed just before measurement operation to form a lithium reagent composition, wherein said lithium reagent composition is an aqueous solution.

18. The lithium reagent kit according to claim 17, a coloring is measured at a wavelength of 530 nm to 560 nm.

19. The lithium reagent kit according to claim 18, wherein the wavelength range is 550 nm.

20. A method for preparing a lithium reagent composition, comprising:

dissolving a compound having a structure represented by the formula (I):

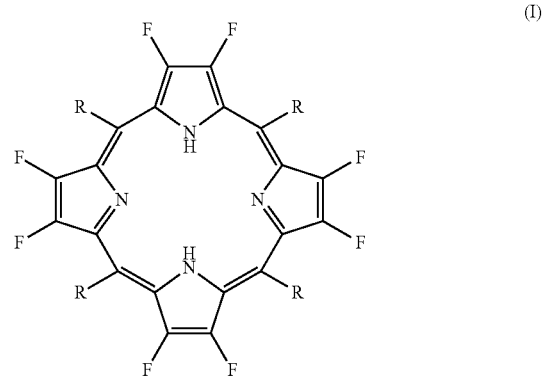

(I)

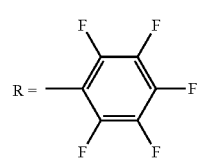

in which all hydrogens bonded to carbons of a tetraphenylporphyrin are replaced by fluorine atoms in a water-miscible organic solvent selected from the group consisting of dimethylsulfoxide (DMS), dimethylformamide (DMF) and dimethylacetamide (DMA), and a pH modifier for adjusting the pH to a range from pH 5 to pH 12 to obtain a mixture, and then adding water to the mixture.

21. A lithium reagent for measuring the quantity of lithium in serum or blood plasma, wherein the lithium reagent is a dilution of a composition comprising a compound having a structure represented by the formula (I):

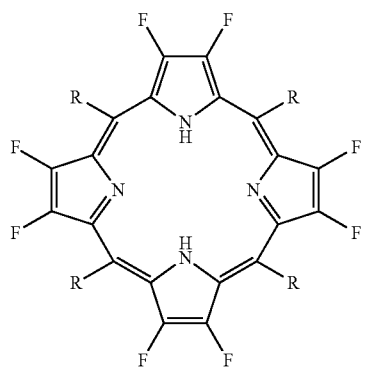

(I)

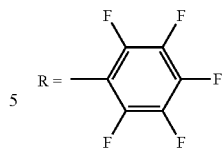

in which all hydrogens bonded to carbons of a tetraphenylporphyrin are replaced by fluorine atoms, a water-miscible organic solvent selected from the group consisting of dimethylsulfoxide (DMS), dimethylformamide (DMF) and dimethylacetamide (DMA), and a pH modifier for adjusting the pH to a range from pH 5 to pH 12, wherein the composition is diluted with 1L of water to obtain the dilution.

22. The lithium reagent of claim 21, wherein the compound having a structure represented by the formula (I) is present in an amount of 0.5 g/L to 1.0 g/L.

* * * * *